United States Patent [19]

Johnson

[11] Patent Number: 5,021,662
[45] Date of Patent: Jun. 4, 1991

[54] METHOD AND APPARATUS FOR REAL-TIME IN-LINE MATERIAL MONITORING

[75] Inventor: Milo R. Johnson, Richardson, Tex.

[73] Assignee: Texas Instruments Incorporated, Dallas, Tex.

[21] Appl. No.: 354,523

[22] Filed: May 19, 1989

[51] Int. Cl.$^5$ .......................................... G01N 21/35
[52] U.S. Cl. .................... 250/339; 250/341; 250/343; 250/358.1; 250/359.1
[58] Field of Search ............... 250/343, 373, 565, 339, 250/341, 359.1, 358.1

[56] References Cited

U.S. PATENT DOCUMENTS

| | | | |
|---|---|---|---|
| 3,218,914 | 11/1965 | Bartz et al. | 326/320 |
| 4,084,906 | 4/1978 | Bibbero | 356/96 |
| 4,227,083 | 10/1980 | Sherinski | 250/343 |
| 4,859,064 | 8/1989 | Messerschmidt et al. | 356/446 |

FOREIGN PATENT DOCUMENTS 2938844  4/1981  Fed. Rep. of Germany ...... 250/339

*Primary Examiner*—Constantine Hannaher
*Attorney, Agent, or Firm*—Melvin Sharp; James T. Comfort; N. Rhys Merrett

[57] ABSTRACT

An apparatus (10) for real-time in-line monitoring of a material (26) comprises a blackbody source (12), a first set of reflective surfaces (17) and a second set of reflective surfaces (38). Electromagnetic radiation (16) is emitted from the blackbody source (12) into the first set of reflective surfaces (17), which directs the radiation to a flow stream or material (26) which is to be tested. The radiation passes through or is reflected from the material (26). A transmission spectrum, resulting from the passage of the radiation through the material (26) or the reflection from the material (26), is then received by the second set of reflective surfaces (38). The second set of reflective surfaces (38) diffracts the transmission spectrum (34-36) and focusses the diffracted spectrum onto a detector (52). The detector (52) provides transmission spectrum data to a microprocessor (58) for comparison to a characteristic spectrum of the material (26) for determination of the necessity of a process adjustment.

25 Claims, 2 Drawing Sheets

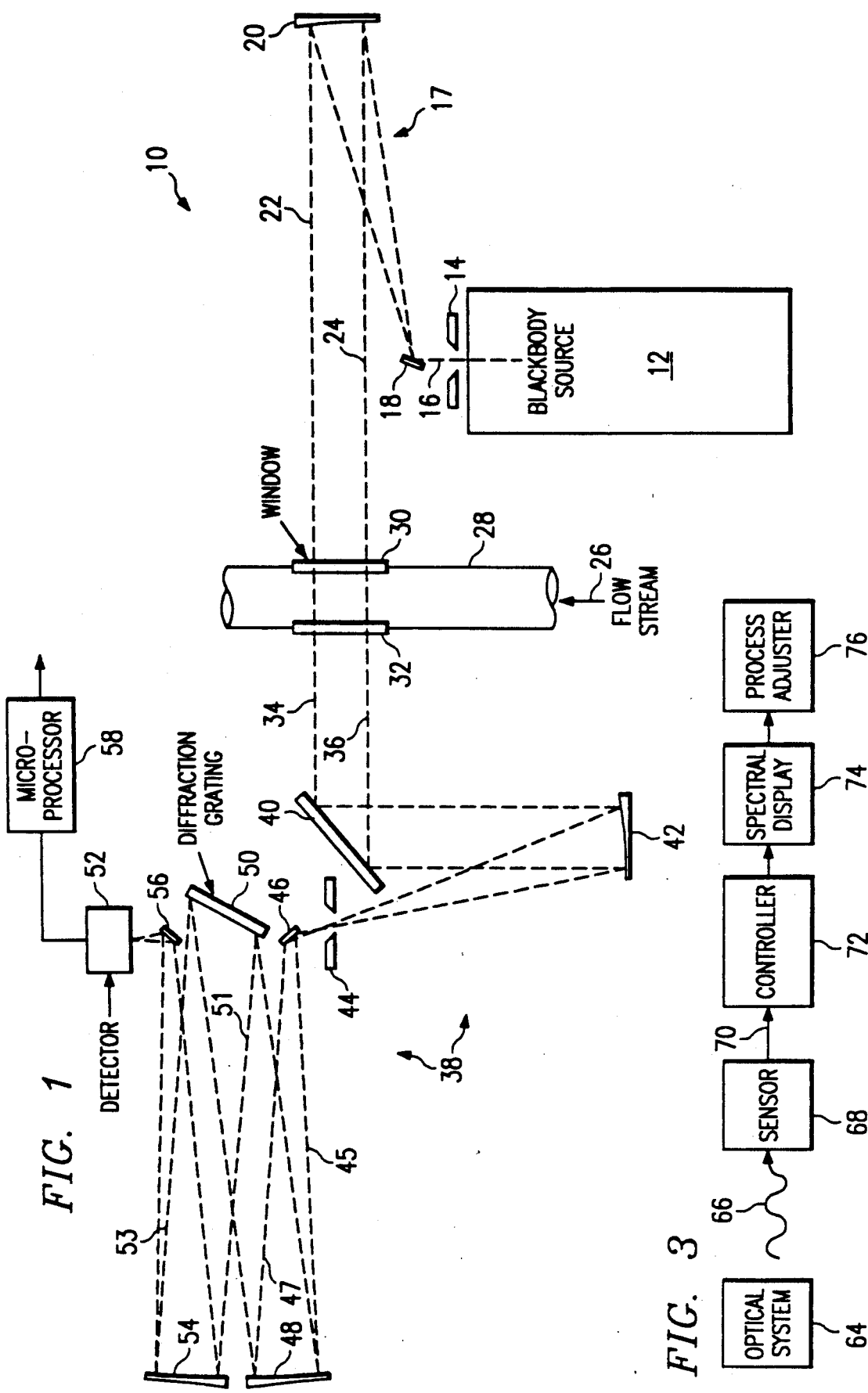

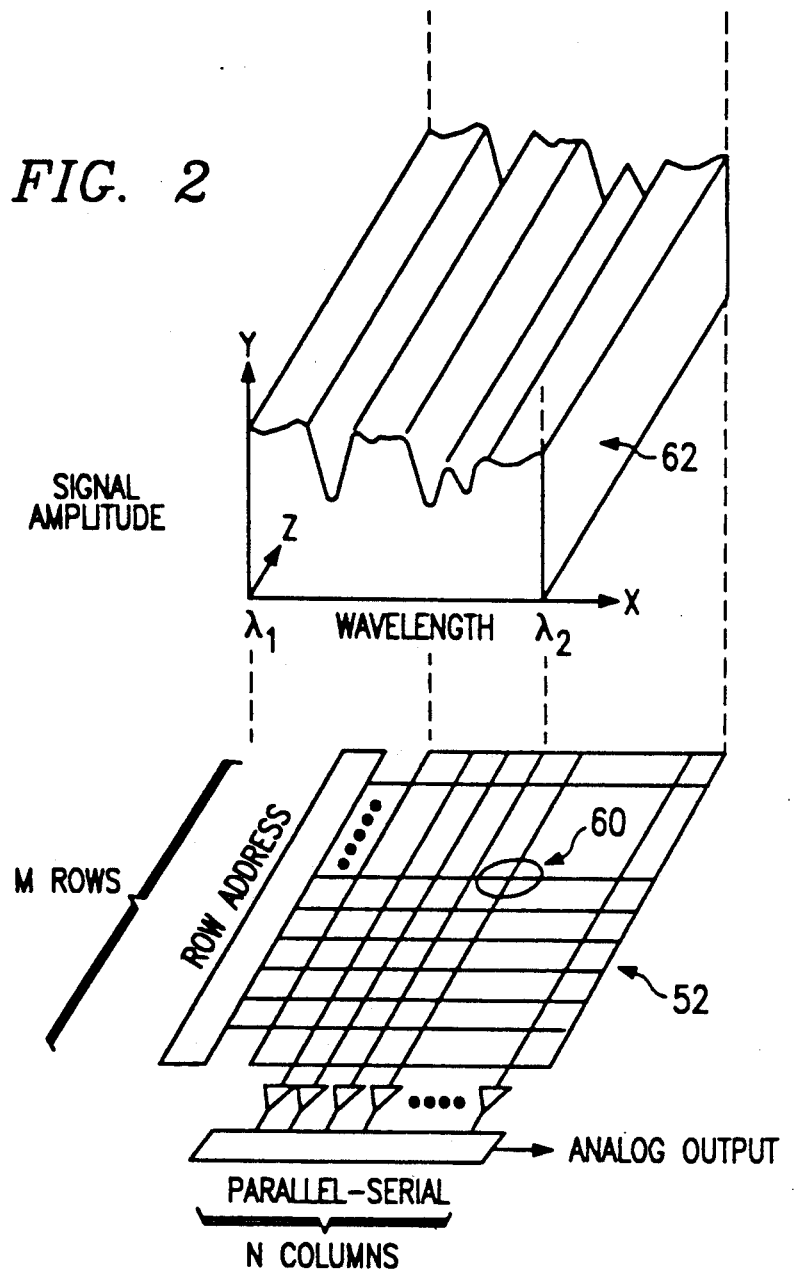

METHOD AND APPARATUS FOR REAL-TIME IN-LINE MATERIAL MONITORING

TECHNICAL FIELD OF THE INVENTION

This invention relates in general to materials monitoring, and in particular to a method and apparatus for real-time in-line material monitoring.

BACKGROUND OF THE INVENTION

In many industries it is necessary to closely monitor the composition or specific properties of a material during processing of the material. For example, during the processing of cheese, it is necessary to monitor the ratios of proteins, oils and water to meet government standards, as well as to make a quality product. Since most materials being processed are constantly changing due to additions of various components, mixing, drying, etc., it can be extremely difficult to monitor quality on a real-time basis.

In current technology, it is frequently necessary to remove a sample from a process line to a testing laboratory to determine these ratios or other characteristics. The test results are generally unavailable for several hours. Therefore, if there is any problem with the target characteristics, another several hours worth of the product may have already been made.

Further sampling must then be obtained from the product that may even be already packaged to determine if the product is within target. If the product is out of limits, it must then be recycled or destroyed in order to prevent violation of Federal packaging laws and/or to prevent customer dissatisfaction. Thus, there is a need for a method and apparatus to allow real-time in-line monitoring of a material during its processing.

SUMMARY OF THE INVENTION

The present invention disclosed herein comprises a method and apparatus for real-time in-line material monitoring which eliminates or substantially reduces problems associated with prior material monitoring. The present invention allows the testing of a material which is being processed without the necessity of removing a sample for testing in another location.

In accordance with one aspect of the invention, an apparatus for real-time in-line material monitoring comprises a source for directing electromagnetic radiation at the material to be tested. A detector then receives either a transmission spectrum or a reflection spectrum from the material after the electromagnetic radiation has either passed through or been reflected from the material to be tested, respectively. The spectrum resulting from passing through or being reflected from the material is then compared to a known value for the material. The spectrum may thus be used to determine whether specified properties of the material being tested are within a required tolerance. If necessary, alterations to the material process may be made based on the spectrum to insure that the material meets specifications.

In accordance with another aspect of the invention, an optical system is provided to direct infrared radiation from an infrared source to the material to be tested and to receive the spectrum after the radiation passes through or is reflected from the material. The optical system passes the spectrum to a detector, which then provides a representation of the transmission spectrum. An electronic signal may then be generated to make any appropriate process adjustments to insure the material meets specifications.

It is a technical advantage of the present invention that it allows real-time in-line monitoring of a changing or moving material. It is a further technical advantage that, based upon the monitoring, the material process may be quickly altered to insure that the material meets specifications.

BRIEF DESCRIPTION OF THE DRAWINGS

For a more complete understanding of the present invention and for further advantages thereof, reference is now made to the following Detailed Description taken in conjunction with the accompanying Drawings in which:

FIG. 1 is a cross-sectional view of an apparatus constructed in accordance with a preferred embodiment of the present invention;

FIG. 2 is a representation of a detector array and its relationship to a transmission or reflection spectrum; and FIG. 3 is a block diagram of a complete system in accordance with the present invention for monitoring and adjusting a material process.

DETAILED DESCRIPTION OF THE INVENTION

Referring to FIG. 1, an apparatus constructed in accordance with the preferred embodiment of the present invention is generally identified by the reference numeral 10. The apparatus 10 comprises an infrared source 12, which may comprise, for example, a blackbody. Electromagnetic radiation is emitted from the blackbody source 12, i.e., infrared radiation, which is passed through a slit 14. The slit 14 images the radiation as indicated by the dashed line 16 onto a first set of reflective surfaces 17.

The first set of reflective surfaces 17 comprises a first mirror 18 which transmits the focussed radiation 16 to a second mirror 20. The second mirror 20 may comprise, for example, an off-axis parabolic mirror, which collimates and reflects the radiation as indicated by dashed lines 22 and 24 toward a material to be tested, which is indicated by a flow stream 26. The flow stream or material 26 passes through, for example only, a stainless steel pipe 28. The pipe 28 is provided with a first window 30 and a second window 32 to allow the radiation 22-24 to pass therethrough.

Depending upon the make-up of the material 26, the radiation 22-24 will either pass through or be reflected from the material 26. Materials, such as material 26, have a known or easily determined absorption factor of radiation. Therefore, radiation may be passed through or reflected from a material and be modified by absorption in the material itself, producing a known spectral display which is representative of the chemical composition of the material.

Thus, according to the embodiment in FIG. 1 the radiation 22-24 passes through the first window 30 and into the material 26 within the pipe 28. A known amount of the radiation 22-24 is absorbed by the material 26, and the transmitted energy as indicated by dashed lines 34 and 36 is then transmitted from the material 26 through the second window 32. The transmitted energy 34-36 then enters a second set of reflective surfaces generally identified by the reference numeral 38.

The second set of reflective surfaces 38 comprises a first mirror 40, which reflects the transmitted energy 34-36 to a second mirror 42. The second mirror 42 may comprise, for example, an off-axis parabolic mirror which focuses the energy 34-36 to a slit 44. The slit 44, which has an opening less than the opening of the slit 14, forms an object which is re-imaged by the remainder of the optical system onto the detector 52. The third mirror 46 reflects the transmitted energy, as indicated by dashed lines 45 and 47, to a fourth mirror 48. The fourth mirror 48, which may comprise an off-axis parabolic mirror, collimates and reflects the transmitted energy 45-47 to a diffraction grating 50.

The diffraction grating 50 is constructed and arranged to diffract the transmitted energy into multiple, adjacent beams of differing spectral content. The diffracted spectrum, as indicated by dashed lines 51 and 53, is relayed from the diffraction grating 50 to a fifth mirror 54, which may also comprise an off-axis parabolic mirror. The fifth mirror 54 reflects the diffracted spectrum 51-53 to a sixth mirror 56, which then refocuses and reflects the diffracted spectrum 51-53 to the detector 52.

The diffraction grating 50 forms multiple images of the slit 44, one image for each resolvable wave length band of the transmission spectrum 34-36. The detector 52 may comprise, for example, an uncooled infrared sensor having a two-dimensional array of approximately one hundred twenty-eight by one hundred twenty-eight detecting elements. The detector 52 receives the diffracted transmission spectrum 51-53 with each appropriate wave length being directed by the sixth mirror 56 to the appropriate detecting element thereon.

A microprocessor 58 then receives output from the detector 52, which is compiled and compared with a previously stored characteristic spectrum of material 26, in order to determine whether an adjustment to the make-up of the material 26 is required. It is important to properly preprogram the microprocessor 58 to have a characteristic transmission spectrum of the material 26 with the proper characteristics. A tolerance range is assigned to provide decision points for when the material 26 must be altered to meet the required specifications. From the microprocessor 58, adjustments, if required, may be made to the material 26 by any appropriate means, not shown. For example, the output of microprocessor 58 may be used to control valves or the like to vary the amount of certain components for material 26.

Although the use of a blackbody source 12 has been disclosed, it should be understood that if certain material being processed has a high enough temperature, e.g. 150°-300° C., the material will radiate its own characteristic spectrum and thus a blackbody source would not be required. This technique could, for example, be used to sense emissions from certain types of polymer processing systems without the requirement of a blackbody source.

Referring to FIG. 2, a simplified illustration of how a detector 52 receives and analyzes a transmission spectrum is shown. The detector 52 has an array of wave length detecting elements, such as identified by the reference numeral 60. The detector 52 has rows M and columns N of detecting elements 60. Directly above the detector 52 is an isometric representation of a transmission spectrum 62 that is viewed by the detector 52. The transmission spectrum 62 is represented by wave lengths $\lambda_1$ to $\lambda_2$ in the X direction, by signal amplitude in the Y direction and by a repetition of the transmission spectrum 62 by the individual detecting elements 60 in each of the N columns of the detector 52 in the Z direction. Therefore, each detecting element 60 in a particular row M receives a specific wave length of the spectrum 62, while the corresponding detecting elements within the same column N receive the same wave length. The detector 52 produces an analog output, which may then be analyzed by a microprocessor (not shown) to present a spectral display. The spectral display may be used to compare with a stored characteristic display of the material being tested to determine whether any process alterations are required.

In the preferred embodiment of the invention, the analog signals from the detector 52 are converted into digital representations. The representations are then subsequently digitally summed to improve the signal-to-noise ratio, and thus the accuracy of the spectrum. Such analog to digital conversion is important as allowing full use of a two-dimensional detector array. Further, all control computations may be made on the basis of digital information. In such case, the stored comparison information is also digital to promote accuracy.

Referring to FIG. 3, a block diagram illustrating the various components of a complete apparatus in accordance with the preferred embodiment of the present invention is illustrated. The optical system 64 is indicative of the first and second sets of reflective surfaces 17 and 38 plus the blackbody source 12 of FIG. 1. An output 66 from the optical system 64 is received by the sensor/detector 68. An output 70 from the sensor/detector 68 is received by a controller/microprocessor 72 which compiles the output 70 and provides analysis to produce a spectral display 74. The spectral display 74 may be a visual representation of a transmission spectrum, which may then be used to determine whether a process adjuster 76 must modify the process to insure the material is within specification tolerances.

Thus, a method and apparatus for allowing real-time in-line monitoring of a material is provided. The apparatus 10 allows monitoring of a material 26, which may be constantly changing in specific characteristics to insure that the material 26 meets specified tolerances. By monitoring in real-time, the apparatus 10 allows modification to the process which provides the various components of the material 26 prior to a loss from the production of out-of-tolerance material.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. Apparatus for real-time in-line material monitoring, comprising:
   a two dimensional detector array for receiving a transmission spectrum emitted from the material;
   SNR circuitry for improving signal-to-noise ratio for said received spectrum by digitally summing multiple replicas of said spectrum detected by said two dimensional array, thereby providing an enhanced spectrum; and
   circuitry for comparing said received enhanced spectrum with a stored characteristic spectrum for the material to ensure the material meets a predetermined specification.

2. The apparatus of claim 1, and further comprising a source of infrared light.

3. The apparatus of claim 2, wherein said infrared light comprises a blackbody source.

4. The apparatus of claim 1, further comprising an optical system for directing electromagnetic radiation to the material and for passing said transmission spectrum to said detector.

5. The apparatus of claim 4, wherein said optical system comprises:
a first set of reflective surfaces for directing said radiation to the material; and
a second set of reflective surfaces for transferring said spectrum to said detector.

6. The apparatus of claim 5, wherein said first set of reflective surfaces comprises:
a slit for imaging said electromagnetic radiation;
a first mirror; and
a second mirror such that said first mirror reflects said electromagnetic radiation to said second mirror which collimates and deflects said radiation to the material.

7. The apparatus of claim 6, wherein said second mirror comprises an off-axis parabolic mirror.

8. The apparatus of claim 5, wherein said second set of reflective surfaces comprises:
a first, second, third, fourth, fifth and sixth mirror;
a slit; and
a diffraction grating such that said first mirror reflects said spectrum from the material to said second mirror, said second mirror reflects said spectrum to said slit, said slit re-images said spectrum and passes said re-imaged spectrum to said third mirror, said third mirror deflects said re-imaged spectrum to said fourth mirror, said fourth mirror collimates said spectrum and directs said collimated spectrum to said diffraction grating, said grating diffracts said spectrum which is then received by said fifth mirror, said fifth mirror deflects said diffracted spectrum to said sixth mirror and said sixth mirror refocuses said spectrum prior to sending the diffracted spectrum to said detector.

9. The apparatus of claim 8, wherein said second, fourth and fifth mirrors comprise off-axis parabolic mirrors.

10. The apparatus of claim 1, wherein said detector comprises an uncooled infrared sensor.

11. Apparatus for real-time in-line material monitoring, comprising:
a source for directing infrared radiation at a moving line of the material;
a two dimensional detector array for receiving a transmission spectrum emitted from the material;
SNR circuitry for improving signal-to-noise ratio for said transmission spectrum by digitally summing multiple replicas of said spectrum detected by said two dimensional array, thereby providing an enhanced transmission spectrum; and
circuitry for comparing said received enhanced transmission spectrum from the material with a previously stored characteristic spectrum for the material, and means responsive to said comparison for varying the composition of the material.

12. The apparatus of claim 11, wherein said source comprises a tungsten-halogen lamp.

13. The apparatus of claim 11, wherein said detector comprises an uncooled infrared sensor.

14. The apparatus of claim 11, further comprising a first set of reflective surfaces for directing said radiation to the material, and means for transferring said radiation to said detector.

15. The apparatus of claim 14, wherein said first set of reflective surfaces comprises:
a slit;
a first mirror; and
a second mirror.

16. The apparatus of claim 14, wherein said means for transferring said spectrum comprises a second set of reflective surfaces.

17. The apparatus of claim 16, wherein said second set of reflective surfaces comprises:
a first, second, third, fourth, fifth and sixth mirror;
a slit; and
a diffraction grating.

18. The apparatus of claim 11, further comprising a controller for analyzing output from said detector to determine if the material meets a prescribed specification.

19. The apparatus of claim 18, further comprising a process adjuster to allow for correction of any variations of said characteristics from said specification.

20. A method for real-time in-line monitoring of a material, comprising the steps of:
emitting a transmission spectrum from the material;
detecting multiple replicas of said spectrum;
digitally summing said replica spectra to improve signal-to-noise ratio, thereby providing an enhanced spectrum; and
comparing said enhanced spectrum with a predetermined target value such that the material is monitored for specified characteristics.

21. The method of claim 20, and further comprising passing electromagnetic radiation through the material.

22. The method of claim 20, and further comprising reflecting electromagnetic radiation from the material.

23. The method of claim 20, wherein the step of comparing further comprises altering the material if said specified characteristics are outside a tolerance range of said predetermined target value.

24. A method for real-time monitoring of a material during processing of the material, comprising the steps of:
transferring electromagnetic radiation from a source to the material;
transferring a transmission spectrum from the material to a two dimensional detector array to provide multiple replicas of said transmission spectrum;
digitally summing said replica transmission spectra to improve signal-to-noise ratio, thereby providing an enhanced transmission spectrum;
detecting variations between said enhanced transmission spectrum and a stored spectrum to reveal specified characteristics of the material; and
varying the processing of the material in response to said detected variations.

25. The method of claim 24, wherein said step of transferring a transmission spectrum comprises breaking radiation emanating from the material into different wave lengths and detecting the amplitude of said different wave lengths.

* * * * *